United States Patent [19]

Biere et al.

[11] Patent Number: 4,757,070
[45] Date of Patent: Jul. 12, 1988

[54] 3-OXADIAZOLYL-5-AMINOALKYL-BETA-CARBOLINE DERIVATIVES COMPOSITIONS AND USE

[75] Inventors: Helmut Biere; Andreas Huth; Dieter Rahtz; Ralph Schmiechen; Dieter Seidelmann; David N. Stephens, all of Berlin, Fed. Rep. of Germany

[73] Assignee: Schering Aktiengesellschaft, Berlin and Bergkamen, Fed. Rep. of Germany

[21] Appl. No.: 130,049

[22] Filed: Dec. 8, 1987

Related U.S. Application Data

[62] Division of Ser. No. 944,165, Dec. 22, 1986, Pat. No. 4,731,365.

[30] Foreign Application Priority Data

Dec. 20, 1985 [DE] Fed. Rep. of Germany ....... 3545776

[51] Int. Cl.⁴ ................ A61K 31/435; A61K 31/535; C07D 471/04
[52] U.S. Cl. ........................... 514/228.2; 514/232.5; 514/232.8; 514/253; 514/292; 544/58.6; 544/60; 544/80; 544/121; 544/126; 544/357; 544/361; 546/87
[58] Field of Search ................ 544/58.6, 80, 121, 126, 544/357, 361, 60; 546/87; 514/222, 230, 232, 234, 253, 242, 227, 237, 239

[56] References Cited

U.S. PATENT DOCUMENTS

4,645,773  2/1987  Engelstoft et al. ................... 546/87

Primary Examiner—Robert W. Ramsuer
Attorney, Agent, or Firm—Millen & White

[57] ABSTRACT

Compounds of formula I

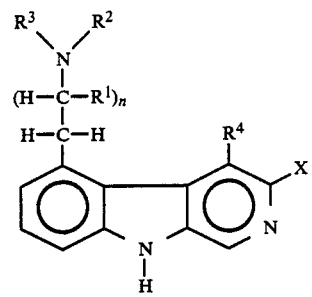

wherein
n is 0 or 1,
$R^1$ is hydrogen or lower alkyl,
$R^2$ and $R^3$ each independently is hydrogen, optionally substituted lower alkyl, acyl or aryl, or together with the nitrogen atom form a 5-6-member heterocycle,
$R^4$ is hydrogen, lower alkyl or lower alkoxyalkyl and
X is $COOR^6$, $CO-NR^7R^8$, or an oxadiazolyl radical of the formula

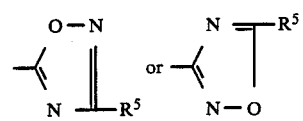

wherein
$R^5$ is H, lower alkyl or cycloalkyl,
$R^6$ is H or lower alkyl,
$R^7$ and $R^8$ each independently is hydrogen, optionally substituted lower alkyl, acyl or aryl, or
$R^7$ and $R^8$ together with the nitrogen atom can form a 5-6-member heterocycle,
are valuable drugs, e.g., have psychotropic activity.

9 Claims, No Drawings

3-OXADIAZOLYL-5-AMINOALKYL-BETA-CARBOLINE DERIVATIVES COMPOSITIONS AND USE

This is a division of application Ser. No. 944,165 filed Dec. 22, 1986 now U.S. Pat. No. 4,731,365.

This invention relates to new 5-aminoalkyl-beta-carboline derivatives, their production and their use as medicines.

The compounds according to the invention have valuable pharmacological properties. They particularly affect the central nervous system and thus are suitable as psychotropic drugs.

The compounds according to the invention have the general formula I

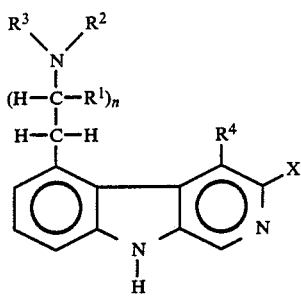

wherein
n is 0 or 1,
$R^1$ is hydrogen or lower alkyl,
$R^2$ and $R^3$ each independently is hydrogen, optionally substituted lower alkyl, acyl or aryl, or together with the nitrogen atom form a 5-6-member heterocycle,
$R^4$ is hydrogen, lower alkyl or lower alkoxyalkyl and X is $COOR^6$, $CO-NR^7R^8$, or an oxadiazolyl radical of the formula

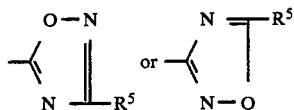

wherein
$R^5$ is H, lower alkyl or cycloalkyl,
$R^6$ is H or lower alkyl,
$R^7$ and $R^8$ each independently is hydrogen, optionally substituted lower alkyl, acyl or aryl, or
$R^7$ and $R^8$ together with the nitrogen atom can form a 5-6-member heterocycle.

Lower alkyl includes both straight-chain and branched radicals of $C_1-C_6$ carbon atoms. For example, preferred $C_{1-4}$ alkyl radicals are methyl, ethyl, n-propyl, isopropyl, n-butyl, isobutyl and tert-butyl. Pentyl and hexyl radicals are also suitable.

Suitable substitutents on the lower alkyl radicals $R^2$, $R^3$, $R^7$ and $R^8$ include: hydroxy, lower alkoxy, mercapto, lower alkylthio, phenyl, amino optionally substituted by lower alkyl or a nitrogen-containing 5-6-member heterocycle (e.g., saturated or unsaturated aliphatic) which also can contain another heteroatom such as sulfur, nitrogen or oxygen, for example, morpholine, piperidine, thiomorpholine, piperazine, pyrrolidine and can be substituted with 1 or 2 lower alkyl groups. In the piperazine radical the nitrogen in the 4-position additionally can be substituted by a lower alkyl radical. Above and below, "lower" refers to 1-6 carbon atoms.

If $R^2$ and $R^3$ or $R^7$ and $R^8$ together with the nitrogen atom form a heterocycle, then the latter is 5-6-membered and can be saturated or unsaturated, e.g., aliphaic or aromatic, and can contain another heteroatom such as sulfur, nitrogen or oxygen. For example, the above-named saturated heterocycles and the following unsaturated heterocycles are suitable: imidazole, pyrazole, pyrrole, etc.

The acyl radicals preferably are alkanoyl derived from an aliphatic carboxylic acid with up to 4 carbon atoms, for example, acetic acid, propionic acid, butyric acid, formic acid, etc.

Aryl includes phenyl and heteroaromatic rings, for example, furan, thiophene, pyridine, etc., e.g., 5 or 6 membered rings containing 1-2 O, N or S atoms.

Lower alkoxyalkyl $R^4$ groups include $C_{1-6}$-alkoxy-$C_{1-6}$-alkyl, where both alkyl portions can be derived from groups such as those mentioned above.

Preferred $R^7$ and $R^8$ groups are $C_{1-3}$ alkyls and 5-6-member nitrogen-containing saturated heterocyclic groups formed together with the nitrogen atom and which can contain another heteroatom.

Cycloalkyl radicals $R^5$ can contain 3-7 carbon atoms. Preferred are those with 3-5 carbon atoms, for example, cyclopropyl, methylcyclopropyl, cyclobutyl, cyclopentyl, etc.

It is known that certain sites in the central nervous system of vertebrates exhibit a great specific affinity for the binding of 1,4- and 1,5-benzodiazepines (Squires, R. F. and Braestrup, C., Nature (London) 266 (1977) 734). These sites are called benzodiazepine receptors. The important receptor affinity for the pharmacological properties of the compounds according to the invention was determined by examination of their capability to displace radioactively marked flunitrazepam from benzodiazepine receptors. The displacement activity of the compounds according to the invention is indicated as $IC_{50}$ and $ED_{50}$ values. The $IC_{50}$ value indicates the concentration which causes a 50% displacement of the specific binding of $H^3$-flunitrazepam (1.0 nM, 0° C.) in samples with a total volume of 0.55 ml of a suspension of brain membranes, e.g., of rats.

The displacement test is performed as follows:

0.5 ml of a suspension of untreated rat forebrain in 25 mM $KH_2PO_4$, pH=7.1 (5-10 mg of tissue/sample) is incubated for 40-60 minutes at 0° C. together with $^3H$-diazepam (specific activity 14.4 Ci/mmol, 1.9 nM) or $^3H$-flunitrazepam (specific activity 87 Ci/mmol, 1.0 nM). After incubation, the suspension is filtered through a glass filter, the residue is washed twice with cold buffer solution and the radioactivity is measured with a scintillation counter.

The test is then repeated, but, before addition of the radioactively marked benzodiazepine, a specific amount or an excess amount of the compound whose displacement activity is to be determined, is added. The $IC_{50}$ value can be calculated on the basis of the values obtained.

The $ED_{50}$ value represents the dose of a test substance which causes a reduction of the specific binding of the flunitrazepam on the benzodiazepine receptor in a live brain to 50% of the control value.

The in vivo test is performed as follows:

The test substance is injected into groups of mice in different doses and normally intraperitoneally. After 15 minutes the $^3$H-flunitrazepam is administered intravenously to the mice. After another 20 minutes the mice are sacrificed, their forebrain is removed and the radioactivity specifically linked to the brain membrane is measured by scintillation counting. The $ED_{50}$ value is determined from the dose/action curves.

In the pharmacological tests, the compounds according to the invention show especially anxiolytic and anticonvulsive effectiveness. For examination of the anticonvulsive action, stopping of the spasms induced by pentylenetetrazole (pentazol) was studied. Pentazol is administered subcutaneously in an amount of 150 mg/kg as a hydrochloric acid solution (pH 2–3) 15–30 minutes after the intraperitoneal application of the test substance. This amount induces clonic and tonic spasms, which lead to death in untreated animals. The number of mice which show spasms and the number of them that died 30 minutes after pentazol are recorded. The $ED_{50}$ values are determined according to the method of Litchfield and Wilcoxon (J. Pharmacol. exp. Ther. 96 (1949) 99–103) as the amount of antagonistically acting substance which protects 50% of the animals from spasms and death.

The new compounds of general formula I have valuable pharmacological properties. They particularly affect the central nervous system and thus are suitable as psychotropic drugs for human medicine. The compounds can be used especially for treatment of anxiety, either alone or accompanied by depressions, epilepsy, sleep disturbances, spasticities and muscle relaxation during anesthesia. Some compounds according to the invention also show amnestic properties and others memory-promoting properties.

The compounds according to the invention can be used for the formulation of pharmaceutical preparations for administration, e.g., to mammals including humans, for example, for oral and parenteral application according to galenic methods known in the art.

Suitable inactive ingredients for formulation of pharmaceutical preparations include those physiologically compatible organic and inorganic vehicles for enteral and parenteral application, which are inert in regard to the compounds according to the invention. Suitable vehicles include, for example, water, salt solutions, alcohols, polyethylene glycols, polyhydroxyethoxylated castor oil, gelatins, lactose, amylose, magnesium stearate, talc, silicic acid, fatty acid mono and diglycerides, pentaerythritol fatty acid ester, hydroxymethylcellulose and polyvinylpyrrolidone. The pharmaceutical preparations can be sterilized and/or mixed with inactive ingredients such as lubricants, preservatives, stabilizers, wetting agents, emulsifiers, buffering agents and dyes. For parenteral application are suitable especially injection solutions or suspensions, especially aqueous solutions of the active compounds in polyhydroxyethoxylated castor oil. For oral application are suitable especially tablets, sugar-coated tablets or capsules with talc and/or a hydrocarbon vehicle or binding agent, such as, for example lactose, corn or potato starch. The administration can take place also in liquid form, as, for example, as juice to which optionally a sweetening agent is added.

The compounds according to the invention can be administered in a dose unit of 0.05 to 100 mg of active substance in a physiologically compatible vehicle. The compounds according to the invention are administered in a dose of 0.1 to 300 mg/day, preferably 1–30 mg/day, e.g., as an anxiolytic, analogously to the known agent diazepam and analogously to clonazepam to treat epilepsy.

The production of the compounds of general formula I takes place according to methods known in the art.

For example, the production of the compounds of formula I can be achieved by (a) reacting a compound of formula II

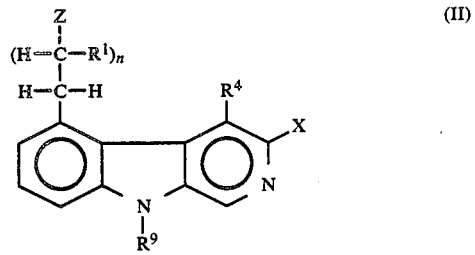

wherein $R^1$, $R^4$, X and n have the meanings indicated above,

Z is halogen or hydroxy and $R^9$ is hydrogen or a protecting group, with a compound $HNR^2R^3$, wherein $R^2$ and $R^3$ have the meanings indicated above, and then optionally cleaving off the protecting group, (b) hydrogenating a compound of formula III

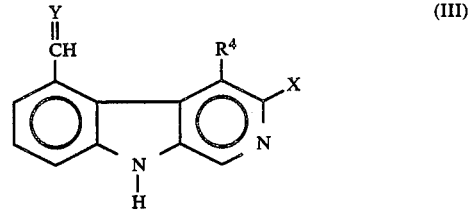

wherein $R^4$ and X have the meanings mentioned above and

Y is an $O_2N$—C—$R^1$— or $R^2N$ group, wherein $R^1$ has the meanings mentioned above and $R^2$ represents optionally substituted lower alkyl or aryl, to a compound of formula I with $R^3$ being hydrogen.

Then, optionally, the compounds obtained according to process (a) or (b) can be transesterified or the ester saponified. Optionally, the carboxylic acid thus obtained is (α) amidated or (β) reacted with a compound

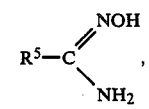

wherein $R^5$ has the meanings mentioned above, to form a compound of formula I in which X is

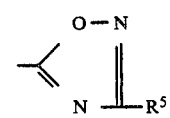

with $R^5$ having the meanings mentioned above, or (c) reacting a compound of formula IV

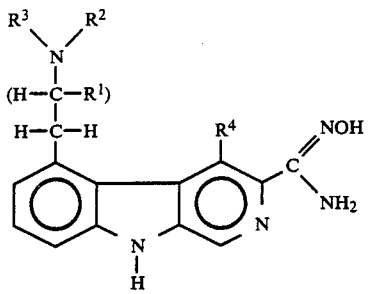 (IV)

wherein
R$^1$, R$^2$, R$^3$, R$^4$ and n have the meanings mentioned above,
with a carboxylic acid anhydride (R$^5$CO)$_2$O, wherein R$^5$ has the meaning mentioned above, to form a compound of formula I in which X is

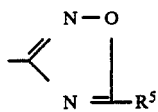

with R$^5$ having the meanings mentioned above.

Introduction of the amino group according to process (a) can, for example, take place by reaction of the corresponding halogen compound with primary or secondary amines. Chlorine, bromine or iodine is suitable as halogen. Suitable as solvents are dipolar aprotic solvents, for example, dimethyl sulfoxide, dimethylformamide, N-methylpyrrolidone, etc., or protic solvents, for example, alcohols such as methanol, ethanol, propanol, etc. or chlorinated hydrocarbons, for example, chloroform, methylene chloride, etc.

Starting from hydroxyalkylene compounds, the corresponding amines can likewise be produced according to the usual methods, for example, by haloalkylene compounds produced intermediately with phosphorous trihalide in the above-mentioned solvents.

Suitable reaction temperatures are from 0° C. to the boiling temperature of the solvent. The reaction is generally ended after about 10 to 24 hours.

If a usual protecting group as, for example, an acyl or tosyl protecting group is present in the 9 position, the group is cleaved off in the reaction with the amine or subsequently removed by the usual methods, for example, by treatment with bases such as sodium or potassium carbonates/hydroxides or alcoholates.

The amination can be performed with or without a protective inert gas, such as argon or nitrogen.

If in process (a) beta-carboline-3-carboxylic acids are used, the corresponding beta-carboline-3-carboxylic acid amides are obtained.

Hydrogenation of the compounds of formula III according to process (b) takes place preferably catalytically, for example, with noble metal catalysts such as platinum or palladium on suitable supports such as carbon or with Raney nickel. Hydrogenation is preferably performed in protic solvents such as alcohols, for example, ethanol, methanol, propanol, etc. at room temperature to the boiling temperature of the solvent under normal pressure or H$_2$ pressure.

To avoid transesterification, the operation is performed in the respective alcohol of the ester component as solvent. The reaction is generally ended after 5 to 7 hours.

According to process (b) primary amines are obtained by hydrogenation of nitro compounds, and secondary amines are obtained by hydrogenation of imines.

If a transesterification is desired, it is possible to react, for example, with the corresponding alcohol or alkali alcoholate. Optionally, titanium tetraisopropylate can be added in water-free alcohol as catalyst. The transesterification usually is performed at temperatures of 60°–120° C. and is ended after about 2–6 hours.

Introduction of the tert-butyl ester group takes place, for example, by reaction of the carboxylic acid with tert-butoxy-bis-(dimethyl-amino)methane. The reaction is generally performed under an inert gas atmosphere such as argon or nitrogen and with exclusion of moisture at elevated temperature.

The saponification of the ester group can take place in an acidic or alkaline manner; preferably it is saponified in an alkaline manner, by the ester being heated to temperatures up to the reflux temperature of the reaction mixture with dilute aqueous lye such as potassium or sodium hydroxide in a protic solvent such as, for example, methanol, ethanol or ethylene glycol.

Carboxylic acid amides are obtained, for example, by reaction with amines of the corresponding imidazolides, which are intermediately produced from carboxylic acids and carbonyldiimidazole or thionyldiimidazole. The reaction is performed at room temperature in dipolar aprotic solvents, for example, dimethylformamide, dimethylacetamide, etc.

For the introduction of the 1,2,4-oxadiazol-5-yl radical the beta-carboline carboxylic acid is brought to condensation, at the reflux temperature of the reaction mixture, with an amidoxime of the formula

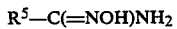

in an inert solvent which boils above 100° C. and is inert in regard to the reactant. Suitable solvents for the condensation reaction are, for example, toluene and dimethylformamide. Appropriately, the free beta-carboline-3-carboxylic acid is suitably activated before the condensation reaction. For this purpose, the free acid can be converted, for example, into the mixed anhydride, into the activated ester or into the chloride. Activation by conversion to an imidazolide with imidazole/thionyl chloride or also carbonyldiimidazole in an aprotic solvent such as dioxane, tetrahydrofuran, dimethylformamide or N-methylpyrrolidone at temperatures between 0° and 50° C., preferably room temperature, has proved successful.

For the introduction of the 1,2,4-oxadiazol-3-yl radical, for example, the beta-carboline-3-carboxamidoxime of formula IV is reacted with the acid anhydride (R$^5$CO)$_2$O at room temperature and then heated to boiling. The reaction is ended after about 7 hours and working up is done according to the usual processes.

The compounds according to the invention can be present racemates or can be separated into their antipodes by the usual processes.

The starting materials are known or can be prepared from known starting materials according to known processes. For example, 3-carboxamidoximes can be produced from beta-carboline carboxylic acids by reacting 3-carboxylic acid nitrile with hydroxylamine. The 5-halomethyl initial compounds of formula II can be prepared, for example, by reaction of 5-methyl carboline compounds with N-halosuccinimide, especially N-bromosuccinimide under the usual reaction conditions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight, unless otherwise indicated.

EXAMPLES

EXAMPLE 1

5-Phenylaminomethyl-beta-carboline-3-carboxylic acid ethyl ester 5-phenyl-iminomethyl-beta-carboline-3-carboxylic acid ethyl ester (0.25 g) is hydrogenated in 100 ml of ethanol with addition of Raney nickel at normal pressure and a temperature of 25° C. Taking up of 1 mol of hydrogen takes about 40 minutes. The residue remaining after filtering of the catalyst and evaporation of the filtrate is chromatographed on silica gel with a mixture of 10 parts of dichloromethane and one part of ethanol. Thus, 0.15 g of phenylaminomethyl-beta-carboline-3-carboxylic acid ethyl ester is obtained.

Melting point 256°–258° C.

The initial product is prepared as follows:

(a)

5-Formyl-beta-carboline-3-carboxylic acid ethyl ester

5-Hydroxymethyl-beta-carboline-3-carboxylic acid ethyl ester (1.0 g) is stirred in dichloromethane (250 ml) with manganese dioxide (1.5 g) for 16 hours at room temperature (25° C.). After addition of more manganese dioxide (0.75 g) the reaction mixture is stirred for another 16 hours. Then after filtering of the undissolved portion it is evaporated, the residue is recrystallized twice from ethyl acetate. Thus, 0.5 g of 5-formyl-beta-carboline-3-carboxylic acid ethyl ester with a melting point of 273°–276° C. is obtained.

(b)

5-Phenyliminomethyl-beta-carboline-3-carboxylic acid ethyl ester

5-Formyl-beta-carboline-3-carboxylic acid ethyl ester (0.153 g) is stirred with aniline (0.112 g) in acetic acid (3 ml) under nitrogen for an hour at 25° C. The precipitated crystals are suctioned off. The yield is 0.111 g of 5-phenyliminomethyl-beta-carboline-3-carboxylic acid ethyl ester with a melting point of 298°–302° C.

EXAMPLE 2

5-(1-Imidazolylmethyl)-4-methoxymethyl-beta-carboline-3-carboxylic acid ethyl ester 5-Bromo-methyl-4-methoxymethyl-beta-carboline-3-carboxylic acid ethyl ester (0.35 g) is left with imidazole (0.13 g) in dimethyl sulfoxide (4 ml) for three days at room temperature. The precipitate resulting after addition of water (40 ml) is recrystallized from ethanol and chromatographed on silica gel with a mixture of 19 parts of dichloromethane and one part of methanol. Thus 0.2 g of 5-(1-imidazolylmethyl)-4-methoxymethyl-beta-carboline-3-carboxylic acid ethyl ester with a melting point of 220°–222° C. is obtained.

The initial material is produced as follows:

(a)

4-Acetoxymethylindole

4-Hydroxymethylindole (17 g) is heated in pyridine (12 ml) with acetic anhydride (11.9 ml) for three hours on the steam bath. After dilution with ether, the reaction mixture is first shaken out with 1N hydrochloric acid, then with saturated sodium bicarbonate solution and finally with water. The ether solution is evaporated. 20 g of 4-acetoxymethylindole remains.

(b)

3-(4-Acetoxymethylindol-3-yl)-4-methoxy-2-nitrobutyric acid ethyl ester

4-Acetoxymethylindole (189 g) is dissolved in a mixture of toluene (6 l) and acetic acid (0.7 l). To this solution is added 3-hydroxy-2-nitro-5-oxa-hexanoic acid ethyl ester (570 ml). The flask containing the mixture is evacuated by means of a water jet pump. Then balancing to normal pressure is brought about by argon. Evacuation and pressure balancing are repeated four times. Then the reaction mixture is refluxed for two hours in a water-free argon atmosphere. After concentrating to 2 l the solution is diluted with ethyl acetate and shaken out three times with a liter of 1N hydrochloric acid each. Then it is washed to neutrality with saturated hydrochloric acid solution. The solution, dried over sodium sulfate, is evaporated. The residue is chromatographed on silica gel with dichloromethane. 393 g of the title compound is obtained in oily form.

(c)

3-(4-Acetoxymethylindol-3-yl)-2-amino-4-methoxy-butyric acid ethyl ester 3-(4-acetoxymethylindol-3-yl)-2-nitro-4-methoxy-butyric acid ethyl ester (226 g) is hydrogenated in ethanol (2.3 l) with Raney nickel as catalyst under hydrogen of normal pressure without addition of heat. 3 mol of hydrogen is taken up in 3½ hours, whereby the temperature reaches a maximum of 45° C. After filtering of the catalyst and evaporation of the residue, the raw product is chromatographed on silica gel with a mixture of dichloromethane (97.5%) and ethanol (2.5%). 130 g of the title compound as noncrystalline diastereomeric mixture is obtained.

(d)

5-Acetoxymethyl-4-methoxymethyl-1,2,3,4-tetrahydro-beta-carboline-1,3-dicarboxylic acid-3 ethyl ester A solution of 3-(4-acetoxymethylindol-3-yl)-2-amino-4-methoxy-butyric acid ethyl ester (8.7 g) in ethyl acetate (40 ml) is slowly added drop by drop to a solution of glyoxylic acid monohydrate (2.4 g) in water (30 ml), cooled to 0° C., under argon protection and with stirring. The pH of the solution is adjusted to 4 by addition of potassium carbonate (about 1 g). Then the mixture is stirred for 2 hours, whereby it is allowed to warm to room temperature. Ethyl acetate and water phases are separated, the water phase is shaken out three times with ethyl acetate. The combined ethyl acetate extracts, for their part, are washed once with water, dried with sodium sulfate and evaporated. 9 g of the title compound remains.

(e)

5-Acetoxymethyl-4-methoxymethyl-beta-carboline-3-carboxylic acid ethyl ester 90% Azodicarboxylic acid diethyl ester (76 ml) without addition of heat with stirring is added drop by drop to a solution of 5-acetoxymethyl-4-methoxymethyl-1,2,3,4-tetrahydro-beta-carboline-1,3-dicarboxylic acid-3-ethyl ester (75 g) in oxygen-free dichloromethane (0.6 l) under argon protection. The temperature rises about 10° C. Reflux is performed for about 9 hours, then the mixture is left at room temperature for 60 hours. The precipitate is suctioned off, further end product can be obtained from the evaporated mother liquor after chromatography on silica gel with a mixture of dichloromethane (95%) with methanol (5%). Altogether 65 g of the title compound in the form of colorless crystals with a melting point of 129°–133° C. is obtained.

(f)

5-Hydroxymethyl-4-methoxymethyl-beta-carboline-3-carboxylic acid ethyl ester 5-Acetoxymethyl-4-methoxymethyl-beta-carboline-3-carboxylic acid ethyl ester (7.9 g) is taken up in a solution of sodium (1.4 g) in ethanol (100 ml) and left for 4 days at +4° C. The solution is concentrated, taken up in abundant ethyl acetate, washed alkali-free with water, dried with sodium sulfate and evaporated in a vacuum. By treatment with ethanol the residue yields 6.6 g of the title compound as colorless crystals with a melting point of 139°–140° C.

(g)

5-Bromo-methyl-4-methoxymethyl-beta-carboline-3-carboxylic acid ethyl ester 5-Hydroxymethyl-4-methoxymethyl-beta-carboline-3-carboxylic acid ethyl ester (1 g) is dissolved in dichloromethane (50 ml). In a dry argon atmosphere a solution of phosphorous tribromide (0.86 g) in dichloromethane (50 ml) is added drop by drop. After 20 hours of stirring at room temperature the resulting precipitate is suctioned off and washed with ethyl acetate. 1.2 g of the title compound, with a melting point of 223°–225° C., is obtained.

EXAMPLE 3

4-Methoxymethyl-5-(4-morpholinylmethyl)-beta-carboline-3-carboxylic acid ethyl ester 5-Hydroxymethyl-4-methoxymethyl-beta-carboline-3-carboxylic acid ethyl ester (0.20 g) is dissolved in dichloromethane (5 ml). A solution of phosphorous tribromide (0.17 g) in dichloromethane (3 ml) is added drop by drop with stirring. After three hours of stirring, the mixture is cooled to +10° C. and mixed with a solution of morpholine (1.0 ml) in ethanol (5 ml) drop by drop. After standing overnight the solvent is evaporated, the residue is chromatographed on silica gel with a mixture of dichloromethane (19 parts) and ethanol (1 part) and the title compound (0.16 g) with a melting point of 195°–196° C. is obtained.

Analogously there is obtained:

4-methoxymethyl-5-(4-methyl-1-piperazinylmethyl)-beta-carboline-3-carboxylic acid ethyl ester, melting point 249°–252° C.

4-methoxymethyl-5-(1-piperidinylmethyl)-beta-carboline-3-carboxylic acid ethyl ester 4-methoxymethyl-5-(2,6-dimethyl-4-morpholinylmethyl)-beta-carboline-3-carboxylic acid ethyl ester 4-methoxymethyl-5-diethylaminomethyl-beta-carboline-3-carboxylic acid ethyl ester 4-methyl-5-(4-morpholinylmethyl)-beta-carboline-3-carboxylic acid ethyl ester
melting point 226°–227° C.

4-methoxymethyl-5-dimethylaminomethyl-beta-carboline-3-carboxylic acid ethyl ester 4-methoxymethyl-5-[2-(4-morpholinyl)-ethyl]-aminomethyl-beta-carboline-3-carboxylic acid ethyl ester 5-[N-(2-ethoxyethyl)-aminomethyl]-4-methoxymethyl-beta-carboline-3-carboxylic acid ethyl ester
melting point 193°–195° C.

5-[N,N-bis(2-methoxyethyl)-aminomethyl]-4-methoxymethyl-beta-carboline-3-carboxylic acid ethyl ester
melting point 103°–105° C.

EXAMPLE 4

4-Methoxymethyl-5-(4-morpholinylmethyl)-beta-carboline-3-carboxylic acid

The ethyl ester (0.30 g) obtained according to example 3 is refluxed in ethanol (30 ml) with 1N of sodium hydroxide solution (2.3 ml) for 4 hours. After cooling, 1N of acetic acid (2.3 ml) is added and evaporated. The crystalline evaporation residue is suctioned off and washed well with water. Thus, 0.27 g of the title compound is obtained.

Melting point 253°–255° C.

Analogously there is produced:

4-methoxymethyl-5-(2,6-dimethyl-4-morpholinylmethyl)-beta-carboline-3-carboxylic acid.

EXAMPLE 5

4-Methoxymethyl-5-(4-morpholinylmethyl)-beta-carboline-3-carboxylic acid tert-butyl ester The acid (0.35 g) obtained according to example 4 is heated in tert-butoxy-bis-(dimethylamino)-methane (7 ml) under argon protection for two hours to 120° C. After evaporation of the tert-butoxy-bis-(dimethylamino)-methane the residue is taken up in ethyl acetate. The solution is shaken out with saturated hydrochloric acid solution, dried and evaporated. The residue is chromatographed on silica gel with a mixture of equal parts of hexane and acetone. The yield of title compound is 0.2 g.

Analogously there is obtained:

4-Methoxymethyl-5-(2,6-dimethyl-4-morpholinylmethyl)-beta-carboline-3-carboxylic acid tert-butyl ester.

EXAMPLE 6

4-Methoxymethyl-5-(4-morpholinylmethyl)-beta-carboline-3-carboxylic acid isopropyl ester 5-Bromo-methyl-4-methoxymethyl-beta-carboline-3-carboxylic acid isopropyl ester (0.53 g) is suspended in ethanol (10 ml). The solution occurring after addition of morpholine (2.6 ml) is allowed to stand for 20 hours at 25° C. Then it is diluted with ethyl acetate (60 ml) and shaken out with water, until it no longer reacts in an alkaline manner. The neutral solution is evaporated in a vacuum, the residue is recrystallized from ethyl acetate. The yield is 0.16 g with a melting point of 214°–216° C.

The initial material is prepared as follows:

(a)

5-Hydroxymethyl-4-methoxymethyl-beta-carboline-3-carboxylic acid isopropyl ester 5-Hydroxymethyl-4-methoxymethyl-beta-carboline-3-carboxylic acid ethyl ester (7.27 g) is refluxed in isopropanol (1000 ml) with titanium tetraisopropylate (7.1 ml) for 5 hours. The solution is evaporated, the residue is dissolved in ethyl acetate. The complete solution is reached by addition of 1N hydrochloric acid. Then it is made alkaline by addition of 1N sodium hydroxide solution. A precipitate resulting thereby is suctioned off. The filtrate is evaporated and yields a residue of 6.0 g of the title compound.

4-Methyl-5-(4-morpholinylmethyl)-beta-carboline-3-carboxylic acid isopropyl ester is analogously obtained from 4-methyl-5-(4-morpholinylmethyl)-beta-carboline-3-carboxylic acid ethyl ester.

(b)

5-Bromomethyl-4-methoxymethyl-beta-carboline-3-carboxylic acid isopropyl ester 5-Hydroxymethyl-4-methoxymethyl-beta-carboline-3-carboxylic acid isopropyl ester (1.0 g) is dissolved in dichloromethane. A solution of 0.83 phosphorous tribromide in 10 ml of dichloromethane is added. After 20 hours the resulting precipitate is suctioned off. The yield is 1.0 g of yellow crystals with indeterminate melting point.

Analogously there are produced:
4-Methoxymethyl-5-(1-pyrrolidinylmethyl)-beta-carboline-3-carboxylic acid isopropyl ester, melting point 173°–174° C.
4-Methoxymethyl-5-(4-thiomorpholinylmethyl)-beta-carboline-3-carboxylic acid isopropyl ester, melting point 217°–219° C.
4-Methoxymethyl-5-(2,6-dimethyl-4-morpholinylmethyl)-beta-carboline-3-carboxylic acid isopropyl ester

EXAMPLE 7

5-morpholino-methyl-beta-carboline-3-carboxylic acid ethyl ester

Under nitrogen, a solution of 0.19 g of 9-acetyl-5-bromoethyl-beta-carboline-3-carboxylic acid ethyl ester in 5 ml of ethanol is mixed with 1 ml of morpholine and stirred overnight at room temperature. After addition of water the crystallizate is suctioned off and recrystallized from ethanol/diethylether. 0.11 g (64%) is obtained. Melting point 285° C.

The initial material is produced in the following way:

A suspension of 6.2 g of 9-acetyl-5-methyl-beta-carboline-3-carboxylic acid ethyl ester (obtained in the usual way from 5-methyl-beta-carboline-3-carboxylic acid ethyl ester by the action of acetic anhydride in pyridine) in 550 ml of carbon tetrachloride is mixed with 4.5 g of N-bromosuccinimide and 0.17 g of azobis(isobutyro)nitrile and radiated with a 500-watt lamp (Nitraphot BT, Osram) for 2 hours, whereby the mixture boils. It is filtered hot and the filtrate is concentrated. The raw product is recrystallized twice from carbon tetrachloride. 5.9 g (75%) of the 5-bromoethyl derivative is obtained.

Melting point 193° C.

Analogously to example 7 there are produced:
5-(4-methylpiperazinylmethyl)-beta-carboline-3-carboxylic acid ethyl ester, melting point 287° C.
5-[N-(1-phenylethyl)-aminomethyl[-beta-carboline-3-carboxylic acid ethyl ester, melting point 232° C.

Analogously to example 7, but in dimethyl sulfoxide as solvent, there is obtained with imidazole:
9-acetyl-5-(1-imidazolylmethyl)-beta-carboline-3-carboxylic acid ethyl ester, melting point 195° C.

EXAMPLE 8

5-(1-Imidazolylmethyl)-beta-carboline-3-carboxylic acid ethyl ester

A suspension of 0.11 g of 9-acetyl-5-(1-imidazolylmethyl)-beta-carboline-3-carboxylic acid ethyl ester in 5 ml of ethanol is mixed with 10 mg of $K_2CO_3$ and refluxed for two hours. After filtering, the solution is concentrated in a vacuum, the residue is mixed with water, suctioned off and recrystallized from water. Yield 70 mg (71%).

Melting point 248° C.

EXAMPLE 9

5-(2-Aminoethyl)-4-methyl-beta-carboline-3-carboxylic acid ethyl ester 5-(2-Nitrovinyl)-4-methyl-beta-carboline-3-carboxylic acid ethyl ester (1 g) is dissolved in ethanol (20 ml) and in a hydrogen atmosphere with stirring is slowly added drop by drop to a suspension of 10% palladium carbon (0.25 g) in ethanol (50 ml) and sulfuric acid (0.1 ml). In the end, it is stirred for another half hour more. Then the catalyst is suctioned off and the filtrate evaporated. After the usual working up, 0.6 g of the title compound is obtained.

The initial compound is prepared as follows:

(a)

5-Formyl-4-methyl-beta-carboline-3-carboxylic acid ethyl ester

The synthesis takes place according to the method described in example 1 from 5-hydroxymethyl-4-methyl-beta-carboline-3-carboxylic acid ethyl ester, which in turn is prepared according to example 2 from 2-nitro-3-hydroxybutyric acid ethyl ester in 5 stages.

(b)

5-(2-Nitrovinyl)-4-methyl-beta-carboline-3-carboxylic acid ethyl ester

A solution of 5-formyl-4-methyl-beta-carboline-3-carboxylic acid ethyl ester (10 g), nitromethane (2 ml) and methylamine hydrochloride (0.2 g) in ethanol (50 ml) is mixed with sodium carbonate (0.3 g) and left for 5 days at 20° C. with occasional shaking. Then it is evaporated to beginning crystallization. 5 g of the title compound crystallizes from the solution cooled with ice water.

EXAMPLE 10

5-(2-aminopropyl)-4-methyl-beta-carboline-3-carboxylic acid ethyl ester

The production takes places analogously to example 9 by condensation of 5-formyl-4-methyl-beta-carboline-3-carboxylic acid ethyl ester with nitroethane and hydrogenation of the resulting 4-methyl-5-(2-nitropropenyl)beta-carboline-3-carboxylic acid ethyl ester.

EXAMPLE 11

4-Methoxymethyl-5-morpholinomethyl-3-(3-ethyl,1,2,4-oxadiazol-5-yl)-beta-carboline A solution of 0.36 g of 4-methoxymethyl-5-morpholinomethyl-beta-carboline-3-carboxylic acid (prepared according to example 4) in 10 ml of absolute dimethylformamide is mixed with 0.2 g of carbonyldiimidazole and stirred for 30 minutes at 60° C. Then 0.4 g of propioamidoxime in 2 ml of DMF is added and the reaction mixture heated to 100° C. for 3 hours. After distilling off of the solvent in a vacuum, the residue is mixed with 20 ml of xylene and refluxed for 3 hours on the water separator, the reaction mixture is filtered hot, the filtrate is concentrated and chromatographed on silica gel. 0.25 g (60%) of oxadiazole derivative is obtained. Melting point 161°–163° C.

4-Methyl-5-(4-morpholinylmethyl)-3-(3-ethyl-1,2,4-(oxadiazol-5-yl)-beta-carboline 4-Methyl-5-(4-morpholinylmethyl-beta-carboline-3-carboxylic acid hydrochloride (0.46 g) is suspended in dimethylformamide (35 ml) and mixed with carbonyldiimidazole (0.46 g). Propionamidoxime (0.5 g) is added to the clear solution after 24 hours at room temperature. The dimethylformamide is distilled off in a vacuum after 48 hours at room temperature. The remaining oil is refluxed in xylene (50 ml) for 3 hours on the water separator, then the xylene is decanted and evaporated. The residue is recrystallized from ethyl acetate.

Yield 0.3 g. Melting point 189°–190° C. The initial material is produced in the following way:

A solution of 4-methyl-5-(4-morpholinylmethyl-beta-carboline-3-carboxylic acid ethyl ester (0.5 g) in ethanol (40 ml) and 1N sodium hydroxide solution (4.3 ml) is refluxed for 4 hours. After cooling, 1N hydrochloric acid (8.7 ml) is added. The solution, clarified by filtering, is left for 2 days at +4° C., then the precipitate resulting during this time is suctioned off. The yield is 0.47 g. Melting point 270°–273° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make numerous changes and modifications of the invention to adapt it to various usages and conditions.

What is claimed is:

1. A 5-Aminoalkyl-beta-carboline of the formula

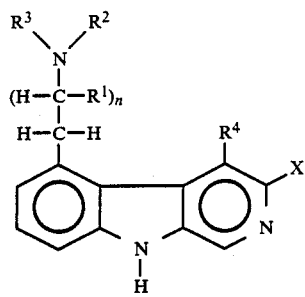

wherein
n is 0 or 1,
$R^1$ is hydrogen or lower alkyl,
$R^2$ and $R^3$ each independently is hydrogen; alkyl; alkyl substituted by OH, lower alkoxy, mercapto, lower alkylthio, phenyl, amino, amino substituted by lower alkyl or a 5-6-member aliphatic N-containing heterocycle which can contain an additional O, N or S atom and can be substituted by 1 or 2 lower alkyl groups; alkanoyl; phenyl; or a 5-6-member aromatic heterocycle containing 1 or 2 O, N or S atoms; or together with the adjoining N-atom $R^2$ and $R^3$ form a 5-6-member aliphatic N-containing heterocycle which can contain an additional O, N or S atom and can be substituted by 1 or 2 lower alkyl groups,
$R^4$ is hydrogen, lower alkyl or lower alkoxy-lower-alkyl and
X is an oxadiazolyl group of the formula

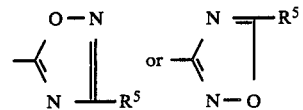

wherein
$R^5$ is H, lower alkyl or $C_{3-7}$-cycloalkyl,
and "lower" refers to 1–6 carbon atoms.

2. A compound of claim 1 wherein $R^2$ and $R^3$ together with the N-atom form said heterocycle.

3. A compound of claim 1 wherein $R^2$ and $R^3$ form morpholino or morpholino substituted by alkyl.

4. A compound of claim 1 wherein $R^2$ and $R^3$ are alkyl or H.

5. 4-methoxymethyl-5-morpholinomethyl-3-(3-ethyl-1,2,4-oxadiazol-5-yl)-beta-carboline.

6. A pharmaceutical composition comprising an amount of a compound of claim 1 and a pharmaceutically acceptable carrier.

7. A composition of claim 6 wherein the amount of said compound is 0.05 to 100 mg.

8. A method of achieving an anxiolytic effect comprising administering to a patient an amount of a compound of claim 1.

9. A method of achieving an anticonvulsive effect comprising administering to a patient an amount of a compound of claim 1.

* * * * *